(12) United States Patent
Kuo

(10) Patent No.: US 8,287,443 B2
(45) Date of Patent: Oct. 16, 2012

(54) THERMOTHERAPY DEVICE

(75) Inventor: Arthur Kuo, Lübeck (DE)

(73) Assignee: Dräger Medical AG & Co. KG, Lübeck (DE)

( * ) Notice: Subject to any disclaimer, the term of this patent is extended or adjusted under 35 U.S.C. 154(b) by 1262 days.

(21) Appl. No.: 12/030,385

(22) Filed: Feb. 13, 2008

(65) Prior Publication Data

US 2008/0207987 A1    Aug. 28, 2008

(30) Foreign Application Priority Data

Feb. 22, 2007  (DE) .......................... 10 2007 008 733

(51) Int. Cl.
*A61G 11/00* (2006.01)
(52) U.S. Cl. ....................................................... 600/22
(58) Field of Classification Search .............. 600/21–22; 5/652.1–652.2, 724, 726; 607/95, 104, 108–112; 62/440–466
See application file for complete search history.

(56) References Cited

U.S. PATENT DOCUMENTS

| | | | | |
|---|---|---|---|---|
| 4,525,884 | A | * | 7/1985 | Tolley ................................ 5/421 |
| 5,935,055 | A | * | 8/1999 | Koch et al. ...................... 600/22 |
| 2008/0234538 | A1 | * | 9/2008 | Lehnhaeuser ................... 600/22 |

FOREIGN PATENT DOCUMENTS

| | | |
|---|---|---|
| DE | 103 13 531 B3 | 6/2004 |
| DE | 103 20 195 B4 | 12/2004 |
| WO | WO 2005/070364 A1 | 8/2005 |
| WO | WO 2005070364 A1 * | 8/2005 |

* cited by examiner

*Primary Examiner* — Charles A Marmor, II
*Assistant Examiner* — Catherine E Burk
(74) *Attorney, Agent, or Firm* — McGlew and Tuttle, P.C.

(57) ABSTRACT

To stabilize the air flow forming an air curtain, a thermotherapy device (1) is provided with air outlet ducts (3) extending at the edge of the reclining surface (2) and with two opposite limiting walls (6, 6'). Each of the two opposite limiting walls (6, 6') is arranged corresponding to the duct width for outflowing air. At least one limiting wall (6, 6') of at least one air outlet duct (3) is provided with a cylinder (5, 5') extending in the direction of flow of the air outlet duct (3) and in parallel to the reclining surface (2) at the discharge-side end, wherein the cylinder (5, 5') has a diameter corresponding to 0.005 to 0.2 times the duct width of the air outlet duct (3). According to a variant, at least one limiting wall (6, 6') of at least one air outlet duct (3) is provided with at least one inner wall (81, 82, 83, 84) forming a nozzle at the discharge-side end. The distance between the limiting wall (6, 6') and the inner wall (81, 82, 83, 84) forming a nozzle with the limiting wall (6, 6') is 0.01 to 0.5 times the duct width of the air outlet duct (3).

20 Claims, 4 Drawing Sheets

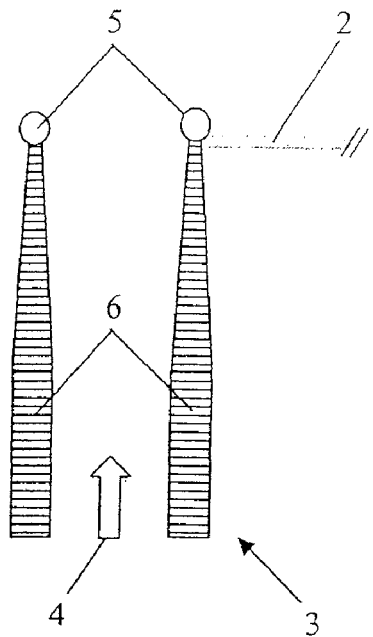
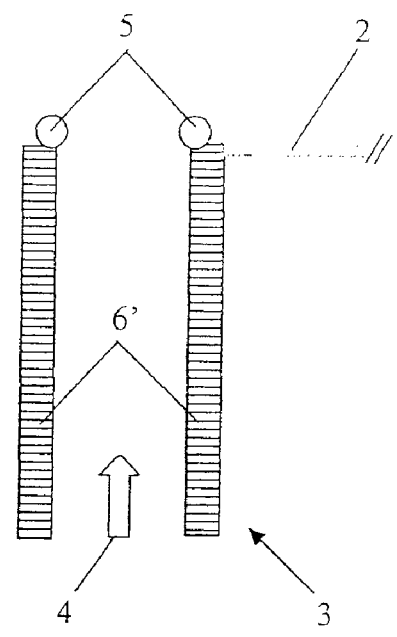
Fig. 2A                Fig. 2B
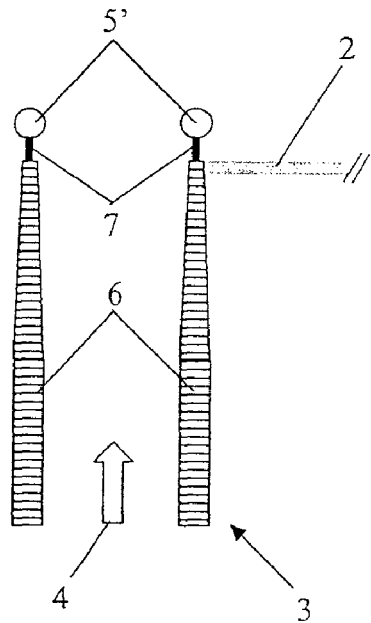
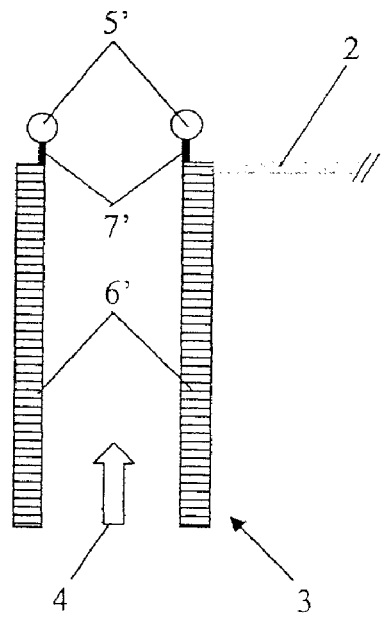
Fig. 2C                Fig. 2D

THERMOTHERAPY DEVICE

CROSS REFERENCE TO RELATED APPLICATIONS

This application claims the benefit of priority under 35 U.S.C. §119 of German Patent Application DE 10 2007 008 733.2 filed Feb. 22, 2007, the entire contents of which are incorporated herein by reference.

FIELD OF THE INVENTION

The present invention pertains to a thermotherapy device with a reclining surface for a patient and with air outlet ducts extending at the edge of the reclining surface with two opposite limiting walls each arranged corresponding to the width of the duct for especially moistened or heated air flowing out.

BACKGROUND OF THE INVENTION

Such thermotherapy devices are used to keep warm and provide air conditioning for especially premature or newborn patients. A thermotherapy device is either a so-called open care unit without a hood or a more or less closed incubator with a hood and with one or more side walls.

Between the two states of a closed incubator and an open care unit, there are so-called hybrids, which are formed by movable elements, for example, by a movable, lowerable hood and/or by removable side walls.

The air-conditioned, i.e., moistened and/or heated air flows form a microclimate in the area of the reclining surface of the thermotherapy device, which microclimate protects the patient from cold and drying out, optionally combined with a heating radiator or with a mattress heater. The stability of the microclimate, which is very important for the patient, strongly depends on the stability of the air flows that are introduced into the thermotherapy device through air outlet ducts.

Air curtains are generated in the prior-art incubators or thermotherapy devices in order to achieve a better insulation effect when, for example, the access windows or a side wall are opened. However, the air curtains and the shear flows generated are not specifically adapted to the particular, currently present wall configuration, e.g., a closed or opened wall, as a consequence of which the microclimate is unstable.

According to the patents DE 103 20 195 B4 and DE 103 13 531 B3, jacketed jets are guided for stabilizing the air curtains, but increased effort is needed for operating and designing such jacketed jets.

SUMMARY OF THE INVENTION

The object of the present invention is therefore to provide a thermotherapy device which extensively prevents shear flows and instability in relation to the air guiding from the air outlet ducts with simple means.

According to one aspect of the invention, a thermotherapy device is provided comprising a patient surface (reclining surface) and air outlet ducts extending at the edge of the patient surface, each of the ducts having a duct width and having two opposite limiting walls. Each of the limiting walls is arranged opposite each other corresponding to the duct width for outflowing air. At least one of the limiting walls of at least one of the air outlet duct is provided, at a discharge-side end thereof, with a cylinder extending in the longitudinal direction of the at least one of the air outlet ducts and in parallel to the patient surface, wherein the cylinder has a diameter corresponding to 0.005 to 0.2 times the duct width of the air outlet duct.

According to another aspect of the invention, a thermotherapy device is provided comprising a patient surface (reclining surface) and air outlet ducts extending at the edge of the patient surface, each of the ducts having a duct width and having two opposite limiting walls. Each of the limiting walls is arranged opposite each other corresponding to the duct width for outflowing air. At least one of the limiting walls of at least one of the air outlet ducts being provided, at a discharge-side end thereof, with at least one inner wall forming a nozzle, a distance between the at least one of the limiting walls and the inner wall forming the nozzle being equal to 0.01 to 0.5 times the duct width of the air outlet duct.

According to still another aspect of the invention, a thermotherapy device is provided comprising a patient surface and air outlet ducts extending at the edge of the patient surface, each of the ducts having a duct width and having two opposite limiting walls. Each of the limiting walls is arranged opposite each other, corresponding to the duct width for outflowing air. At least one of the limiting walls of at least one of the air outlet duct being provided, at a discharge-side end thereof, with a nozzle forming structure comprising at least one of:
  a cylinder extending in the longitudinal direction of the at least one of the air outlet ducts and in parallel to the patient surface, wherein the cylinder has a diameter corresponding to 0.005 to 0.2 times the duct width of the air outlet duct and
  at least one inner wall forming a nozzle, a distance between the at least one of the limiting walls and the inner wall forming the nozzle being equal to 0.01 to 0.5 times the duct width of the air outlet duct.

As a result of features according to the invention, instabilities in the air curtain are absorbed as a whole and shear flows are stabilized with the features proposed.

The cylinder may advantageously be arranged on only one of the limiting walls. The cylinder may be arranged centrally on the at least one of the limiting walls or respectively centrally on each of the two limiting walls. The cylinder may also be arranged offset in a width direction of the air outlet duct.

Support elements may be provided wherein each of the cylinders is held by one of the support elements. Each of the support elements may be attached to the end of a respective limiting wall at a distance equaling at most the duct width.

A distance between the limiting walls may advantageously be from about 5 mm to 30 mm.

The length of each inner wall, when viewed in the direction of flow of air flowing out of the at least one of the air outlet ducts may advantageously correspond at least to half the duct width between the limiting walls.

The distance between the limiting wall and the inner wall may form a flat two-dimensional nozzle, the distance decreasing continuously or piece by piece when viewed in the direction of flow of air flowing out of the at least one of the air outlet ducts.

The inner wall forming a nozzle may be arranged only on the limiting wall located at a greater distance from the patient surface.

Exemplary embodiments will be explained below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

BRIEF DESCRIPTION OF THE DRAWINGS

In the drawings:

FIG. 2A is a sectional view through an air outlet duct of a thermotherapy device with cylinders at a discharge-side end;

FIG. 2B is a sectional view through another air outlet duct of the thermotherapy device with cylinders at a discharge-side end arranged offset in a direction of the air outlet duct;

FIG. 2C is a sectional view through an air outlet duct of another thermotherapy device with support elements and cylinders at a discharge-side end;

FIG. 2D is a sectional view through another air outlet duct of the thermotherapy device with support elements and cylinders at a discharge-side end;

DESCRIPTION OF THE PREFERRED EMBODIMENTS

Figure 1:
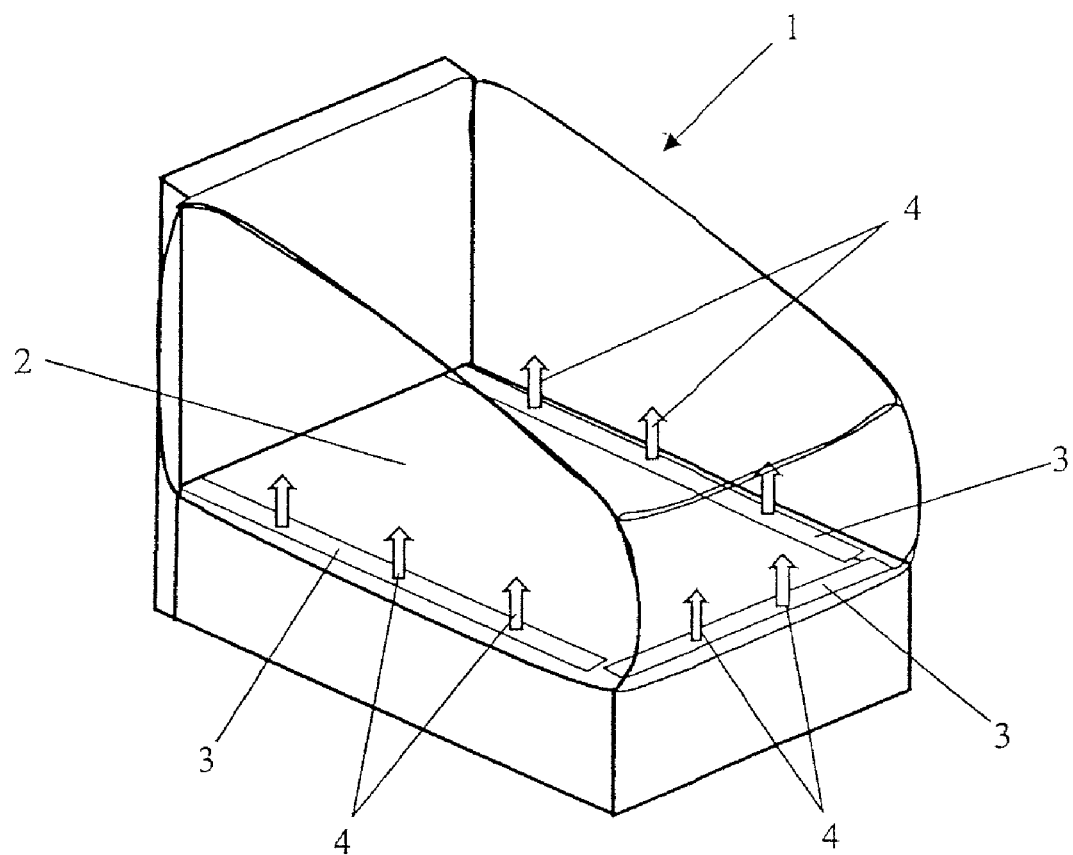
FIG. 1 is a perspective view showing a thermotherapy device according to the embodiments of the invention.
Figure 3A:
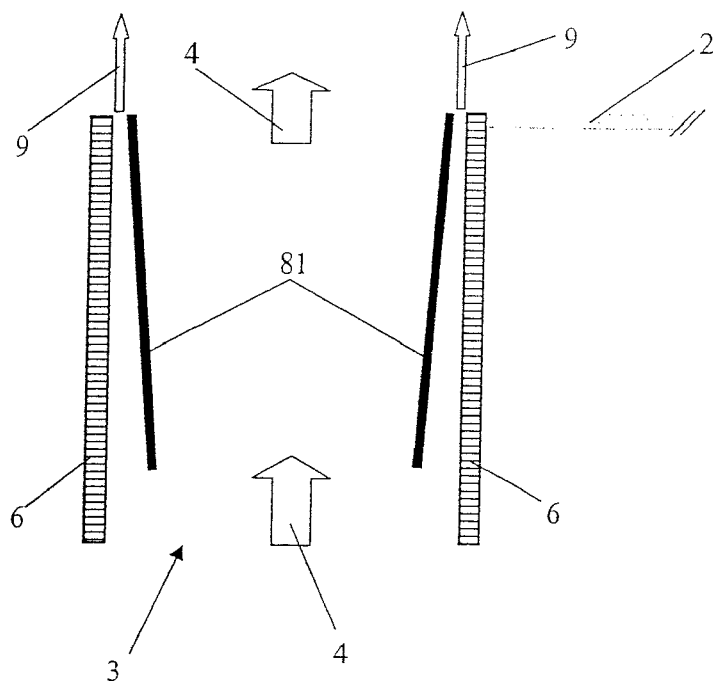
FIG. 3A is a sectional view through an air outlet duct of a thermotherapy device with nozzle forming inner wall at a discharge-side end.
Figure 3B:
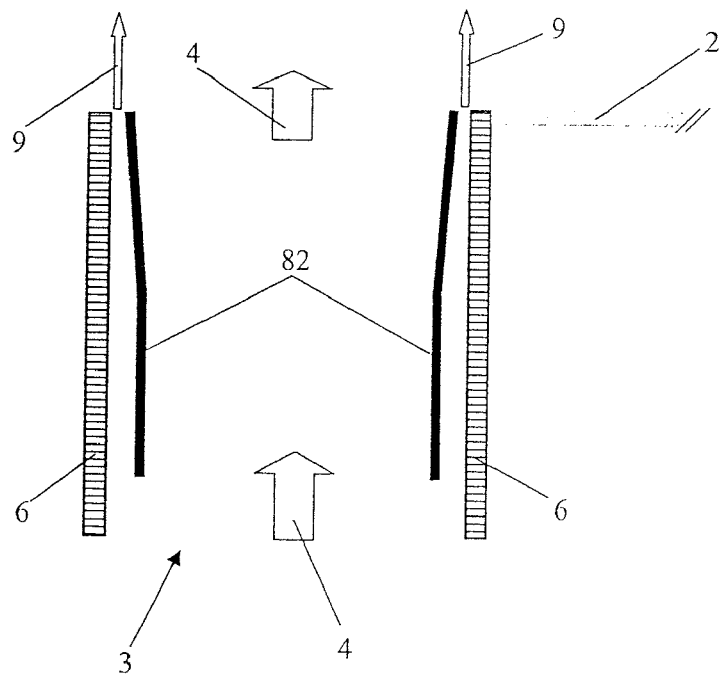
FIG. 3B is a sectional view through another air outlet duct of the thermotherapy device with nozzle forming inner wall at a discharge-side end.
Figure 3C:
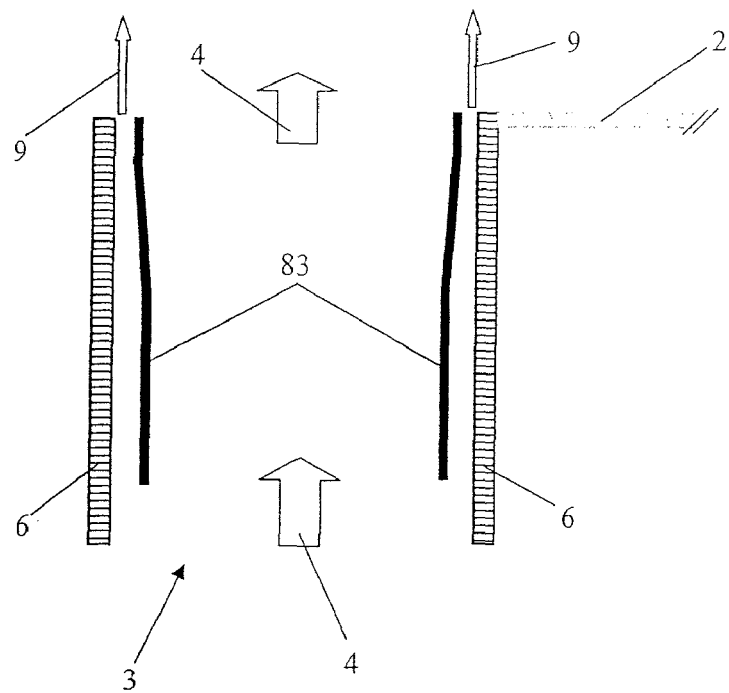
FIG. 3C is a sectional view through an air outlet duct of another thermotherapy device with nozzle forming inner wall at a discharge-side end.
Figure 3D:
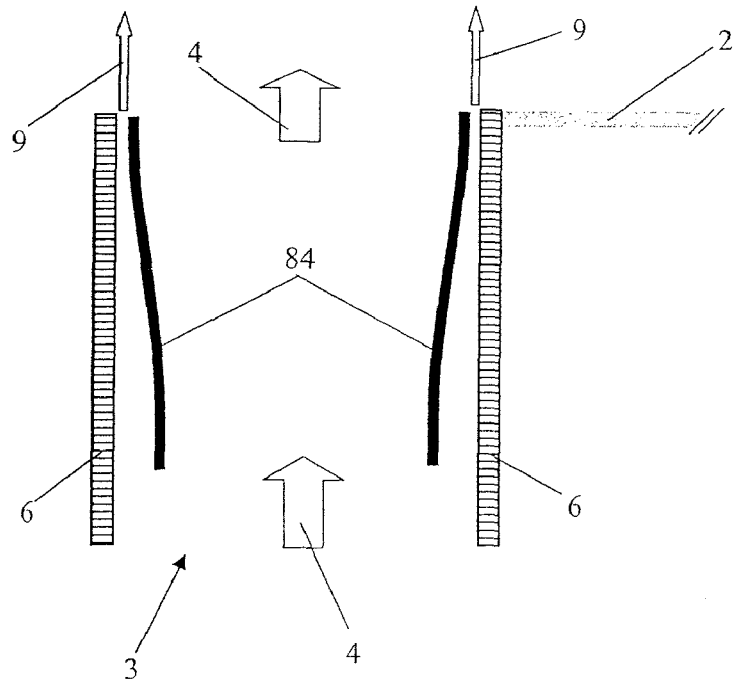
FIG. 3D is a sectional view through another air outlet duct of the thermotherapy device with nozzle forming inner wall at a discharge-side end of FIG. 3C.

Referring to the drawings in particular, FIG. 1 shows a thermotherapy device 1 with a reclining surface (patient surface) 2 and with continuous air outlet ducts 3 extending around the reclining surface 2 on the longitudinal sides and on the foot side with air-conditioned, i.e., moist and heated air being discharged in the direction of flow 4 indicated by the arrows. The outlet ducts 3 of the thermotherapy device 1 may be in the form shown in any of FIGS. 2A-3D and may be comprised of combinations of the shown outlet ducts 3 (e.g., different duct sections having different forms such as the sides and the front being different).

FIG. 2A-D show aspects of a first embodiment type of the air outlet ducts 3 with a cylinder 5, 5' each extending in the longitudinal direction of the air outlet ducts 3 and in parallel to the reclining surface 2 at the discharge-side end of the limiting walls 6, 6'. The cylinder 5, 5' has a diameter of 0.005 to 0.2 times the duct width of the air outlet duct 3.

The cylinders 5, 5' are arranged either directly at one or both limiting walls 6, 6' (FIGS. 2A and 2B) or are made in one piece with these or are attached to the limiting walls 6, 6' by means of support elements 7, 7' at a distance equaling at most the duct width (FIGS. 2C and 2D). The cylinders 5, 5' are preferably arranged centrally on the limiting wall or on each of the two limiting walls 6, 6' (FIGS. 2A and 2C) or in a decentralized position in the direction of the air outlet duct 3 (FIGS. 2B and 2D).

The cylinders 5, 5' act on the air flowing past in the direction of flow 4 and absorb the global instability of the air, as a result of which the propagation of the shear flow and the swirling and mixing thereof are suppressed.

FIGS. 3A through 3D show a second embodiment type of the air outlet ducts 3, wherein at least one limiting wall 6, 6' of at least one air outlet duct 3 is provided, corresponding to the direction of flow 4 of the air, with at least one inner wall 81, 82, 83, 84, which forms a nozzle with a parallel discharge flow 9 at the upper, discharge-side end. The distance between the limiting wall 6, 6' and the inner wall 81, 82, 83, 84 forming a nozzle with the limiting wall 6, 6' equals approx. 0.01 to 0.5 times the duct width of the air outlet duct 3.

The four different embodiments according to FIGS. 3A through 3D show that the distance between the limiting wall 6, 6' and the inner wall 81, 82, 83, 84 forming a flat, two-dimensional nozzle with the limiting wall 6, 6' in the direction of flow 4 is designed such that it decreases in some sections continuously and in some sections in pieces (incrementally). The wall 81, 82, 83 according to FIGS. 3A through 3C has, for example, a plurality of sections that are straight in some parts, or it corresponds, according to FIG. 3D with the wall 84, to the course of an elongated L or S curve.

The velocity of the air volume flow in the direction of flow 4 in and out of the air outlet ducts 3 equals approximately 0.1 m/sec to 1 m/sec.

While specific embodiments of the invention have been shown and described in detail to illustrate the application of the principles of the invention, it will be understood that the invention may be embodied otherwise without departing from such principles.

What is claimed is:

1. A thermotherapy device comprising:
a patient surface for a reclining patient;
air outlet ducts extending at an edge of said patient surface, each of said ducts having a duct width and having two opposite limiting walls extending along a duct longitudinal direction, each of said limiting walls being arranged opposite each other corresponding to the duct width and having a duct discharge-side end for outflowing air defining an outflow air duct width, at least one of said limiting walls of at least one of said air outlet ducts being provided, at the discharge-side end thereof, with a cylinder extending in the duct longitudinal direction of said at least one of said air outlet ducts and in parallel to said patient surface, wherein said cylinder has a diameter corresponding to 0.005 to 0.2 times the outflow air duct width of said air outlet duct and wherein said cylinder suppresses swirling and mixing of outflowing air.

2. A thermotherapy device in accordance with claim 1, wherein said cylinder is arranged on only one of said limiting walls.

3. A thermotherapy device in accordance with claim 1, wherein said cylinder is arranged centrally on said at least one of said limiting walls or respectively centrally on each of said two limiting walls.

4. A thermotherapy device in accordance with claim 1, wherein said cylinder is arranged offset in a width direction of said air outlet duct.

5. A thermotherapy device in accordance with claim 1, further comprising support elements wherein each of said cylinders is held by one of said support elements, each of said support elements being attached to the end of a respective said limiting wall at a distance from the end of a respective said limiting wall equaling at most the duct width.

6. A thermotherapy device in accordance with claim 1, wherein a distance between said limiting walls is from about 5 mm to 30 mm.

7. A thermotherapy device comprising:
a patient surface for a reclining patient; and air outlet ducts extending at an edge of said patient surface, each of said ducts having a duct width and having two opposite limiting walls extending along a duct longitudinal direction, each of said limiting walls being arranged opposite each other corresponding to a duct width for outflowing air, at least one of said limiting walls of at least one of said air outlet ducts being provided inside the duct, at a discharge-side end thereof, with at least one inner wall forming a nozzle, a distance between said at least one of said limiting walls and said inner wall forming said nozzle being equal to 0.01 to 0.5 times the outflow air duct width of said air outlet duct.

8. A thermotherapy device in accordance with claim 7, wherein the length of each said inner wall, when viewed in the direction of flow of air flowing out of the at least one of said air outlet ducts, corresponds at least to half the duct width between said limiting walls.

9. A thermotherapy device in accordance with claim 7, wherein the distance between said limiting wall and said inner wall forms a flat two-dimensional nozzle, said distance decreasing continuously or piece by piece when viewed in the direction of flow of air flowing out of the at least one of said air outlet ducts.

10. A thermotherapy device in accordance with claim 7, wherein said inner wall forming a nozzle is arranged only on said limiting wall located at a greater distance from said patient surface.

11. A thermotherapy device in accordance with claim 7, wherein a distance between said limiting walls is from about 5 mm to 30 mm.

12. A thermotherapy device comprising:
a patient surface;
air outlet ducts extending at an edge of said patient surface, each of said ducts having a duct width and having two opposite limiting walls extending along a duct longitudinal direction corresponding to a duct length for outflowing air, each of said limiting walls being arranged opposite each other corresponding to a duct width and having a duct discharge-side end for outflowing air defining an outflow air duct width, at least one of said limiting walls of at least one of said air outlet ducts being provided, at a discharge-side end thereof, with a nozzle forming structure comprising at least one of:
a cylinder extending in the duct longitudinal direction of said at least one of said air outlet ducts and in parallel to said patient surface, wherein said cylinder has a diameter corresponding to 0.005 to 0.2 times the outflow air duct width of said at least one of said air outlet ducts and said cylinder suppresses swirling and mixing of outflowing air; and
at least one inner wall extending, inside the duct, in the duct longitudinal direction of said at least one of said air outlet ducts and forming a nozzle, a distance between said at least one of said limiting walls and said inner wall forming said nozzle being equal to 0.01 to 0.5 times the outflow air duct width of said air outlet duct.

13. A thermotherapy device in accordance with claim 12, wherein said cylinder is arranged on only one of said limiting walls.

14. A thermotherapy device in accordance with claim 12, wherein said cylinder is arranged centrally on said at least one of said limiting walls or respectively centrally on each of said two limiting walls.

15. A thermotherapy device in accordance with claim 12, wherein said cylinder is arranged offset in a width direction of said air outlet duct.

16. A thermotherapy device in accordance with claim 12, further comprising support elements wherein each of said cylinders is held by one of said support elements, each of said support elements being attached to the end of a respective said limiting wall at a distance equaling at most the duct width.

17. A thermotherapy device in accordance with claim 12, wherein the length of each said inner wall, when viewed in the direction of flow of air flowing out of the at least one of said air outlet ducts, corresponds at least to half the duct width between said limiting walls.

18. A thermotherapy device in accordance with claim 12, wherein the distance between said limiting wall and said inner wall forms a flat two-dimensional nozzle, said distance decreasing continuously or piece by piece when viewed in the direction of flow of air flowing out of the at least one of said air outlet ducts.

19. A thermotherapy device in accordance with claim 12, wherein said inner wall forming a nozzle is arranged only on said limiting wall located at a greater distance from said patient surface.

20. A thermotherapy device in accordance with claim 12, wherein a distance between said limiting walls is from about 5 mm to 30 mm.

* * * * *